United States Patent
Kasemi et al.

(10) Patent No.: US 10,301,423 B2
(45) Date of Patent: May 28, 2019

(54) AMINE FOR LOW-EMISSION EPOXY RESIN COMPOSITIONS

(71) Applicant: SIKA TECHNOLOGY AG, Baar (CH)

(72) Inventors: Edis Kasemi, Zürich (CH); Andreas Kramer, Zürich (CH); Ursula Stadelmann, Zürich (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

(21) Appl. No.: 15/500,441

(22) PCT Filed: Aug. 7, 2015

(86) PCT No.: PCT/EP2015/068302
§ 371 (c)(1),
(2) Date: Jan. 30, 2017

(87) PCT Pub. No.: WO2016/023839
PCT Pub. Date: Feb. 18, 2016

(65) Prior Publication Data
US 2017/0218114 A1    Aug. 3, 2017

(30) Foreign Application Priority Data
Aug. 13, 2014  (EP) ..................... 14180869

(51) Int. Cl.
| | | |
|---|---|---|
| *C08G 59/50* | (2006.01) | |
| *C09D 163/00* | (2006.01) | |
| *C08L 63/00* | (2006.01) | |
| *C07C 211/27* | (2006.01) | |
| *C08G 59/24* | (2006.01) | |

(52) U.S. Cl.
CPC ........ *C08G 59/5033* (2013.01); *C07C 211/27* (2013.01); *C08G 59/245* (2013.01); *C08L 63/00* (2013.01); *C09D 163/00* (2013.01)

(58) Field of Classification Search
CPC .......................... C08G 59/5033; C08G 59/245
See application file for complete search history.

(56) References Cited

U.S. PATENT DOCUMENTS

| | | |
|---|---|---|
| 2014/0107313 A1 | 4/2014 | Burckhardt et al. |
| 2014/0288247 A1* | 9/2014 | Burckhardt .......... C08G 59/184 525/523 |

FOREIGN PATENT DOCUMENTS

| | | | |
|---|---|---|---|
| EP | 2 752 403 A1 | | 7/2014 |
| WO | 2013068502 | * | 5/2013 |

OTHER PUBLICATIONS

Feb. 16, 2018 Chilean Office Action issued in Patent Application No. 2017000361.
Sep. 18, 2015 International Search Report issued in International Patent Application No. PCT/EP2015/068302.
Feb. 14, 2017 International Preliminary Report on Patentability issued in International Patent Application No. PCT/EP2015/068302.
Jun. 19, 2018 Office Action issued in Australian Application No. 2015303289.
Sep. 18, 2018 Office Action issued in Chinese Patent Application No. 201580050994.0.
G. Cignarella et al., "Synthesis and Configuration of trans-1-amino-4-benzyl-2,6-dimethylpiperazine as an Intermediate of Semi-synthetic Rifamycins,"Journal of Heterocyclic Chemistry, vol. 11, No. 6, Dec. 1974, pp. 985-989.
Dec. 5, 2018 Office Action Issued in Colombian Patent Application No. NC2017/0001949.

* cited by examiner

*Primary Examiner* — Kuo Liang Peng
(74) *Attorney, Agent, or Firm* — Oliff PLC

(57) ABSTRACT

An amine of the formula (I) for use as hardener for epoxy resins, hardeners for epoxy resins containing the amine of the formula (I) and resultant epoxy resin compositions which more particularly can be used as low-emission room-temperature-curing epoxy-resin coatings with high hardness and surface quality. The amine of the formula (I) has little odor and is a very successful diluent for epoxy resin compositions. It is more particularly obtained by reductive alkylation from 1,2-propylenediamine and an aldehyde or ketone.

16 Claims, No Drawings

AMINE FOR LOW-EMISSION EPOXY RESIN COMPOSITIONS

TECHNICAL FIELD

The invention pertains to the field of amines, hardeners for epoxy resins, epoxy resin compositions, and their use, particularly as coating, covering or paint.

PRIOR ART

Epoxy resin compositions that are suitable for coating purposes are to have an extremely low viscosity so that they can be processed effectively at ambient temperature. They are also to cure very rapidly and without disruption, even under humid and cold conditions, while forming an even surface without hazing, speckling or craters. Lastly, a fully cured coating is to possess high hardness with low brittleness, in order to withstand mechanical stressing as effectively as possible. For optically demanding applications, such as top coverings on floors, for example, a coating, moreover, is to exhibit high gloss and as little as possible a tendency toward yellowing under the effect of light. Prior-art hardeners for epoxy resin coatings typically comprise adducts of polyamines with epoxides, more particularly with liquid bisphenol resins. Such adducts do permit rapid curing, but are of very high viscosity, this being the reason that in order to formulate a manageable viscosity, the hardeners customarily include considerable proportions of unadducted polyamines and/or diluents. The unadducted polyamines typically have an intense odor and are a cause of increased incidence of blushing effects. "Blushing effects" are surface deficiencies which appear in the course of curing, such as hazing, speckles, roughness, and stickiness, and are caused by formation of salts ("blushing") between amines and carbon dioxide ($CO_2$) from the air, and occur particularly at high atmospheric humidity and low temperatures. The diluents typically lessen the blushing effects and enhance surface quality and coating brittleness, but are not incorporated into the resin matrix on curing and may be released by processes of evaporation or diffusion. Nowadays, however, the desire is increasingly for low-emission products which have a low content of releasable substances after curing. For low-emission epoxy resin compositions, therefore, diluents, such as benzyl alcohol, for example, can be used only in small quantities or not at all.

US 2014/0107313 and EP 2 752 403 disclose amines which are effective diluents of epoxy resin compositions and have hardly any tendency toward blushing effects. As far as curing rate and/or yellowing of the resultant epoxy resin compositions are concerned, however, these amines are still capable of being improved.

SUMMARY OF THE INVENTION

It is an object of the present invention, therefore, to provide a low-odor amine for use in hardeners of room temperature-curing epoxy resin compositions, this amine exerting a strongly diluting effect and allowing access to low-emission epoxy resin coatings having good processing qualities, these coatings curing with sufficient rapidity even under cold conditions and producing coatings of high hardness, good surface quality and low yellowing tendency.

This object is achieved with the amine of the formula (I) as described in claim 1. The amine of the formula (I) is low in odor and exerts a surprisingly highly diluting effect on the epoxy resins that are customarily used, without triggering blushing effects or incompatibilities. It allows access to low-emission epoxy resin coatings having excellent processing qualities, which cure surprisingly quickly, even at relatively low temperatures, such as for example at 8° C., while possessing a surprisingly high ultimate hardness and a glossy, even, nonsticky surface without hazing, speckling or craters, this surface surprisingly, exhibiting virtually no yellowing under the influence of light.

The amine of the formula (I) can be used in particular as a constituent of hardeners which would otherwise, without the use of diluents, be too high in viscosity for coating applications. The amine of the formula (I) can be used with particular advantage together with further amines, more particularly together with amine-functional adducts of polyamines and epoxides. Such hardeners are surprisingly of low viscosity and cure surprisingly rapidly.

Further aspects of the invention are subjects of the further independent claims. Particularly preferred embodiments of the invention are subjects of the dependent claims.

EMBODIMENTS OF THE INVENTION

A subject of the invention is the use of an amine of the formula (I) as hardener for epoxy resins,

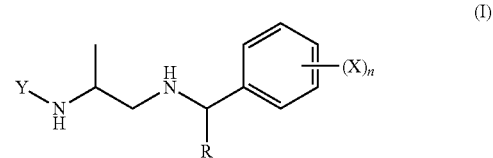

(I)

where
n is 0 or 1 or 2 or 3,
R is a hydrogen radical or is methyl or phenyl,
X is identical or different radicals selected from the group consisting of alkyl, alkoxy and dialkylamino having in each case 1 to 18 carbon atoms, and
Y is a hydrogen radical or a radical of the formula

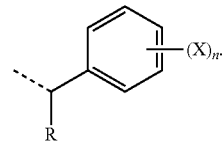

Substance names beginning with "poly", such as polyamine, polyol or polyepoxide, denote substances which formally contain per molecule two or more of the functional groups that occur in their name.

A "primary amino group" is an $NH_2$ group which is bonded to an organic radical, and a "secondary amino group" is an NH group which is bonded to two organic radicals, which may also together be part of a ring.

The "amine hydrogen" refers to the hydrogen atoms of primary and secondary amino groups.

"Amine hydrogen equivalent weight" is the weight fraction of a hardener or of an amine per amine hydrogen present in the hardener or amine.

An "unincorporable diluent" is a substance which is soluble in an epoxy resin and lowers its viscosity and which is not incorporated covalently into the resin matrix when the epoxy resin is cured.

The term "viscosity" in the present document refers to the dynamic viscosity or shear viscosity, which is defined by the ratio between the shearing stress and the shear rate (rate gradient) and is determined as described in the working examples.

A dashed line in the formulae in this document represents in each case the bond between a substituent and the remainder of the associated molecule.

"Molecular weight" is understood in the present document to be the molar mass (in grams per mole) of a molecule. "Average molecular weight" is the numerical average $M_n$ of an oligomeric or polymeric mixture of molecules, and is determined customarily by means of gel permeation chromatography (GPC) against polystyrene as standard.

"Room temperature" refers to a temperature of 23° C.

Preferably n is 0 or 1 or 2, more preferably 0 or 1. These amines allow access to particularly low-viscosity epoxy resin compositions.

An amine in which n is 0 is a particularly effective diluent.

An amine in which n is 1 is particularly low in odor and, according to the group X, may allow particularly rapid curing and/or particularly effective dilution.

Most preferably n is 0.

Preferably X is identical or different radicals selected from the group consisting of alkyl, alkoxy and dialkylamino having in each case 1 to 12, more particularly 1 to 4, carbon atoms. More preferably X is methyl or is methoxy or is dimethylamino.

Preferably Y is a hydrogen radical. These amines allow access to particularly low-viscosity epoxy resin compositions having particularly rapid curing.

Preferably R is a hydrogen radical or is methyl, and more particularly is a hydrogen radical. These amines allow access to particularly low-viscosity epoxy resin compositions.

Particularly preferred is an amine of the formula (I) wherein Y is a hydrogen radical and n is 0. These amines are accessible with particular simplicity and allow access to particularly low-viscosity epoxy resin compositions which cure very rapidly.

Particularly preferred, furthermore, is an amine of the formula (I) in which Y is a hydrogen radical, n is 1 and X is methoxy or is dimethylamino. These amines allow access to epoxy resin compositions having particularly rapid curing. The methoxy group or the dimethylamino group is preferably in para-position.

Especially preferred amines of the formula (I) are selected from the group consisting of $N^1$-benzyl-1,2-propanediamine, $N^1$-(4-isopropylbenzyl)-1,2-propanediamine, $N^1$-(4-tert-butylbenzyl)-1,2-propanediamine, $N^1$-(4-methoxybenzyl)-1,2-propanediamine, $N^1$-(4-(dimethylamino)benzyl)-1,2-propanediamine, $N^1$-(1-phenylethyl)-1,2-propanediamine, $N^1$-benzhydryl-1,2-propanediamine, $N^1$-(1-(4'-methyl)phenylethyl)-1,2-propanediamine and $N^1$-(1-(4'-methoxy)phenylethyl)-1,2-propanediamine.

Especially preferred among these is $N^1$-benzyl-1,2-propanediamine. In this case, Y and R are each a hydrogen radical and n is 0. This amine allows access to low-odor and low-emission epoxy resin compositions of especially low viscosity, with rapid development of hardness or curing, and with surprisingly high hardness, which exhibit hardly any blushing-related surface defects even under damp and cold conditions and which, surprisingly, exhibit virtually no yellowing.

Also especially preferred among these is $N^1$-(4-methoxybenzyl)-1,2-propanediamine. In this case, Y and R are each a hydrogen radical, n is 1 and X is a methoxy radical in position 4. This amine allows access to low-emission and low-odor epoxy resin compositions with very low viscosity, particularly rapid development of hardness or curing, and high hardness, which exhibit virtually no blushing-related surface defects even under damp and cold conditions and which, surprisingly, exhibit virtually no yellowing.

Also especially preferred among these is $N^1$-(4-(dimethylamino)benzyl)-1,2-propanediamine. In this case, Y and R are each a hydrogen radical, n is 1 and X is a dimethylamino radical in position 4. This amine allows access to low-emission and low-odor epoxy resin compositions with very low viscosity, very particularly rapid development of hardness or curing, and particularly high hardness, which exhibit virtually no blushing-related surface defects even under damp and cold conditions and which, surprisingly, exhibit virtually no yellowing.

The amine of the formula (I) is preferably obtained from the reductive alkylation of 1,2-propylenediamine with at least one aldehyde or ketone of the formula (II) and hydrogen. Reaction products obtained therefrom have a high content of amines of the formula (I) and are particularly suitable for use as hardeners for epoxy resins.

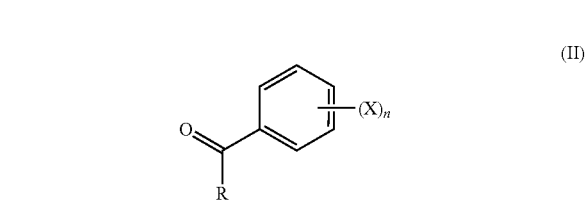

(II)

In the formula (II), R, X and n have the definitions already stated.

The reductive alkylation may take place directly with molecular hydrogen or indirectly by hydrogen transfer from other reagents, such as formic acid, for example. With preference, molecular hydrogen is used. Reaction conditions are advantageously selected such that one or both amino groups of 1,2-propylenediamine are singularly alkylated with high selectivity and the benzene ring is not hydrogenated.

The reaction is carried out preferably at a temperature of 40 to 120° C. and in the presence of a suitable catalyst. Preferred as catalyst are palladium on carbon (Pd/C), platinum on carbon (Pt/C), Adams catalyst or Raney nickel, more particularly palladium on carbon or Raney nickel.

When using molecular hydrogen, operation takes place preferably in a pressurized apparatus under a hydrogen pressure of 5 to 150 bar, more particularly 10 to 100 bar.

Preparing the amine of the formula (I) by reductive alkylation in the manner described is particularly advantageous for use as hardener for epoxy resins, because primary amino groups are singularly alkylated with high selectivity, whereas secondary amino groups are barely alkylated further. The product from the preparation process described can therefore be used without further processing as hardener for epoxy resins in the manner described.

In one preferred embodiment, 1,2-propylenediamine is used at a molar ratio of approximately 1/1 relative to the aldehyde or ketone of the formula (II). In that case the 1,2-propylenediamine is preferably dissolved in a solvent which is removed by distillation after the reaction. This preparation is particularly economical. An amine of the formula (I) prepared in this way includes not only monoalkylated 1,2-propylenediamine (amine of the formula (I)

where Y is a hydrogen radical) but also a certain fraction of N,N'-dialkylated 1,2-propylenediamine (amine of the formula (I) where Y is a radical of the formula

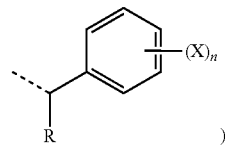

and possibly further alkylation products.

Examples of further alkylation products possibly present are depicted in the following formulae.

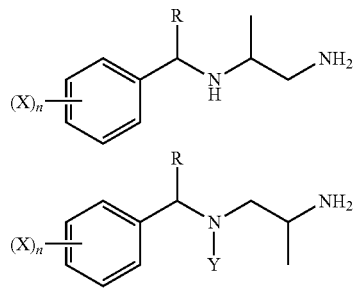

In another preferred embodiment, 1,2-propylenediamine is used in a stoichiometric excess over the aldehyde or ketone of formula (II). The molar ratio between 1,2-propylenediamine and the aldehyde or ketone of the formula (II) is preferably at least 2/1, more particularly at least 3/1. The excess 1,2-propylenediamine is removed before or preferably after the reduction, in particular by distillation. An amine of the formula (I) prepared in this way has a particularly high fraction of monoalkylated 1,2-propylenediamine, i.e., of amine of the formula (I) where Y is a hydrogen radical. In use in accordance with the invention it is notable for a particularly strong diluting effect.

In a further preferred embodiment, 1,2-propylenediamine is used in a stoichiometric deficit relative to the aldehyde or ketone of the formula (II). The molar ratio between 1,2-propylenediamine and the aldehyde or ketone of the formula (II) in this case is preferably 1/1.1 to 1/2, more particularly 1/1.2 to 1/1.9, preferably 1/1.3 to 1/1.8. Here, 1,2-propylenediamine is preferably dissolved in a solvent which is removed by distillation after the reaction. An amine of the formula (I) prepared in this way has an increased fraction of N,N'-dialkylated 1,2-propylenediamine. This has the advantage that its amine hydrogen equivalent weight is comparatively high, producing particularly effective dilution for the same level of addition of amine hydrogens.

Suitability as aldehyde of the formula (II) is possessed in particular by benzaldehyde, 2-methylbenzaldehyde (o-tolualdehyde), 3-methylbenzaldehyde (m-tolualdehyde), 4-methylbenzaldehyde (p-tolualdehyde), 2,5-dimethylbenzaldehyde, 4-ethylbenzaldehyde, 4-isopropylbenzaldehyde (cuminaldehyde), 4-tert-butylbenzaldehyde, 2-methoxybenzaldehyde (o-anisaldehyde), 3-methoxybenzaldehyde (m-anisaldehyde), 4-methoxybenzaldehyde (anisaldehyde), 2,3-dimethoxybenzaldehyde, 2,4-dimethoxybenzaldehyde, 2,5-dimethoxybenzaldehyde, 3,4-dimethoxybenzaldehyde (veratraldehyde), 3,5-dimethoxybenzaldehyde, 2,4,6-trimethylbenzaldehyde, 2,4,5-trimethoxybenzaldehyde (asaronaldehyde), 2,4,6-trimethoxybenzaldehyde, 3,4,5-trimethoxybenzaldehyde or 4-dimethylaminobenzaldehyde. Preferred are benzaldehyde, 4-isopropylbenzaldehyde (cuminaldehyde), 4-tert-butylbenzaldehyde, 4-methoxybenzaldehyde (anisaldehyde) or 4-dimethylaminobenzaldehyde.

Suitability as ketone of the formula (II) is possessed in particular by acetophenone, benzophenone, 2'-methylacetophenone, 3'-methylacetophenone, 4'-methylacetophenone, 2'-methoxyacetophenone, 3'-methoxyacetophenone, 4'-methoxyacetophenone, 2',4'-dimethylacetophenone, 2',5'-dimethylacetophenone, 3',4'-dimethylacetophenone, 3',5'-dimethylacetophenone, 2',4'-dimethoxyacetophenone, 2',5'-dimethoxyacetophenone, 3',4'-dimethoxyacetophenone, 3',5'-dimethoxyacetophenone, 2',4',6'-trimethylacetophenone or 2',4',6'-trimethoxyacetophenone. Preferred are acetophenone, benzophenone, 4'-methylacetophenone or 4'-methoxyacetophenone. Particularly preferred is acetophenone.

Particularly preferred as aldehyde or ketone of the formula (II) is benzaldehyde, 4-methoxybenzaldehyde or 4-dimethylaminobenzaldehyde.

Most preferred is benzaldehyde.

One embodiment uses a mixture of two or more different aldehydes or ketones of the formula (II) for the reaction, more particularly a mixture of benzaldehyde and 4-methoxybenzaldehyde or 4-dimethylaminobenzaldehyde.

The amine of the formula (I) is used more preferably as a reaction product from the reductive alkylation of 1,2-propylenediamine with at least one aldehyde or ketone of the formula (II) and hydrogen, as described above, where the 1,2-propylenediamine is used in a stoichiometric excess over the carbonyl groups of the aldehyde or ketone of the formula (II) and where the excess is removed by distillation after the reduction. The ratio between the number of 1,2-propylenediamine molecules and the number of carbonyl groups is preferably at least 2/1, more particularly at least 3/1, more preferably at least 4/1.

With especial preference the reaction product is purified by distillation. In that case the reaction product is distilled and the distillate obtained is used.

A distillate of this kind allows access to low-odor and low-emission epoxy resin compositions of very low viscosity, with rapid development of hardness or curing, and with surprisingly high hardness, these compositions exhibiting virtually no blushing-related surface defects even under damp and cold conditions, and, surprisingly, exhibiting virtually no yellowing.

A distillate of this kind typically consists primarily of the product of the invention alkylated on the $N^1$ nitrogen, and includes fractions of product alkylated on the $N^2$ nitrogen; in other words, in particular, it consists primarily of $N^1$-benzyl-1,2-propanediamine with fractions of $N^2$-benzyl-1,2-propanediamine, or primarily of $N^1$-(4-methoxybenzyl)-1,2-propanediamine with fractions of $N^2$-(4-methoxybenzyl)-1,2-propanediamine, or primarily of $N^1$-(4-(dimethylamino)benzyl)-1,2-propanediamine with fractions of $N^2$-(4-(dimethylamino)benzyl)-1,2-propanediamine.

In a hardener for epoxy resins, the amine of the formula (I) is used preferably in combination with further amines and/or accelerators.

A further subject of the invention, accordingly, is a hardener for epoxy resins, comprising at least one amine of the formula (I) and at least one further amine and/or at least one accelerator. The further amine in this case is not an amine of the formula (I). A hardener of this kind has particularly high reactivity toward epoxy resins.

Suitable accelerators are substances which accelerate the reaction between amino groups and epoxide groups, more particularly acids or compounds which can be hydrolyzed to acids, more particularly organic carboxylic acids such as acetic acid, benzoic acid, salicylic acid, 2-nitrobenzoic acid, lactic acid, organic sulfonic acids such as methanesulfonic acid, p-toluenesulfonic acid or 4-dodecylbenzenesulfonic acid, sulfonic esters, other organic or inorganic acids such as, in particular, phosphoric acid, or mixtures of the aforementioned acids and acid esters; tertiary amines such as, in particular, 1,4-diazabicyclo[2.2.2]octane, benzyldimethylamine, α-methylbenzyldimethylamine, triethanolamine, dimethylaminopropylamine, imidazoles such as, in particular, N-methylimidazole, N-vinylimidazole or 1,2-dimethylimidazole, salts of such tertiary amines, quaternary ammonium salts, such as, in particular benzyltrimethylammonium chloride, amidines such as, in particular, 1,8-diazabicyclo[5.4.0]undec-7-ene, guanidines such as, in particular, 1,1,3,3-tetramethylguanidine, phenols, especially bisphenols, phenolic resins or Mannich bases such as, in particular, 2-(dimethylaminomethyl)phenol, 2,4,6-tris(dimethylaminomethyl)phenol or polymers of phenol, formaldehyde and N,N-dimethyl-1,3-propanediamine, phosphites such as, in particular, diphenyl or triphenyl phosphites, or compounds containing mercapto groups. Preferred accelerators are acids, tertiary amines or Mannich bases.

Most preferred is salicylic acid or 2,4,6-tris(dimethylaminomethyl)phenol or a combination thereof.

Especially suitable as further amine are polyamines which have at least two, more particularly at least three, amine hydrogens reactive toward epoxide groups, more particularly the following polyamines:

reaction products from the reductive alkylation of 1,2-propylenediamine with an aldehyde or ketone of the formula (II) wherein the $N^2$ nitrogen atom is alkylated, such as, in particular, $N^2$-benzyl-1,2-propanediamine, $N^2$-(4-methoxybenzyl)-1,2-propanediamine, $N^2$-(4-(dimethylamino)benzyl)-1,2-propanediamine, $N^2$-(1-phenylethyl)-1,2-propanediamine, $N^2$-benzhydryl-1,2-propanediamine, $N^2$-(1-(4'-methyl)phenylethyl)-1,2-propanediamine or $N^2$-(1-(4'-methoxy)phenylethyl)-1,2-propanediamine;

further aliphatic, cycloaliphatic or arylaliphatic primary diamines, especially 2,2-dimethyl-1,3-propanediamine, 1,3-pentanediamine (DAMP), 1,5-pentanediamine, 1,5-diamino-2-methylpentane (MPMD), 2-butyl-2-ethyl-1,5-pentanediamine (C11-neodiamine), 1,6-hexanediamine, 2,5-dimethyl-1,6-hexanediamine, 2,2(4),4-trimethylhexamethylenediamine (TMD), 1,7-heptanediamine, 1,8-octanediamine, 1,9-nonanediamine, 1,10-decanediamine, 1,11-undecanediamine, 1,12-dodecanediamine, 1,2-, 1,3- or 1,4-diaminocyclohexane, bis(4-aminocyclohexyl)methane ($H_{12}$-MDA), bis(4-amino-3-methylcyclohexyl)methane, bis(4-amino-3-ethylcyclohexyl)methane, bis(4-amino-3,5-dimethylcyclohexyl)methane, bis(4-amino-3-ethyl-5-methyl-cyclohexyl)methane, 1-amino-3-aminomethyl-3,5,5-trimethylcyclohexane (isophoronediamine or IPDA), 2- or 4-methyl-1,3-diaminocyclohexane or mixtures thereof, 1,3-bis(aminomethyl)cyclohexane, 1,4-bis(amino-methyl)cyclohexane, 2,5(2,6)-bis(aminomethyl)bicyclo[2.2.1]heptane (NBDA), 3(4),8(9)-bis(aminomethyl)tricyclo[5.2.1.0$^{2,6}$]decane, 1,4-diamino-2,2,6-trimethylcyclohexane (TMCDA), 1,8-menthanediamine, 3,9-bis(3-aminopropyl)-2,4,8,10-tetraoxaspiro[5.5]undecane, 1,3-bis(amino-methyl)benzene (MXDA) or 1,4-bis(aminomethyl)benzene;

aliphatic, cycloaliphatic or arylaliphatic primary triamines, especially 4-aminomethyl-1,8-octanediamine, 1,3,5-tris(aminomethyl)benzene, 1,3,5-tris(aminomethyl)cyclohexane, tris(2-aminoethyl)amine, tris(2-amino-propyl)amine or tris(3-aminopropyl)amine;

aliphatic primary di- or triamines containing ether groups, especially bis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine or higher oligomers of these diamines, bis(3-aminopropyl)polytetrahydrofurans or other polytetrahydrofurandiamines, cycloaliphatic ether group-containing diamines from the propoxylation and subsequent amination of 1,4-dimethylolcyclohexane, obtainable in particular as Jeffamine® RFD-270 (from Huntsman), or polyoxyalkylenedi- or -triamines, which typically represent products from the amination of polyoxyalkylenedi- or -triols and are obtainable, for example, under the name Jeffamine® (from Huntsman), under the name Polyetheramine (from BASF) or under the name PC Amine® (from Nitroil). Especially suitable polyoxyalkylenedi- or -triamines are Jeffamine® D-230, Jeffamine® D-400, Jeffamine® D-2000, Jeffamine® EDR-104, Jeffamine® EDR-148, Jeffamine® EDR-176, Jeffamine® T-403, Jeffamine® T-3000, Jeffamine® T-5000, or corresponding amines from BASF or Nitroil;

polyamines containing secondary amino groups having two primary aliphatic amino groups, such as, in particular, 3-(2-aminoethyl)aminopropylamine, bis(hexamethylene)triamine (BHMT), diethylenetriamine (DETA), triethylenetetramine (TETA), tetraethylenepentamine (TEPA), pentaethylenehexamine (PEHA) or higher homologs of linear polyethyleneamines such as polyethylenepolyamine having 5 to 7 ethyleneamine units (referred to as "higher ethylenepolyamine", HEPA), products from the multiple cyanoethylation or cyanobutylation and subsequent hydrogenation of primary di- and polyamines having at least two primary amino groups, such as dipropylenetriamine (DPTA), N-(2-aminoethyl)-1,3-propanediamine (N3-amine), N,N'-bis(3-aminopropyl)ethylenediamine (N4-amine), N,N'-bis(3-aminopropyl)-1,4-diaminobutane, N5-(3-aminopropyl)-2-methyl-1,5-pentanediamine, N3-(3-aminopentyl)-1,3-pentanediamine, N5-(3-amino-1-ethylpropyl)-2-methyl-1,5-pentanediamine or N, N'-bis(3-amino-1-ethylpropyl)-2-methyl-1,5-pentanediamine;

polyamines having one or two secondary amino groups, especially products from the reductive alkylation of primary aliphatic polyamines with aldehydes or ketones, especially N-benzyl-1,3-bis(aminomethyl)benzene, N,N'-dibenzyl-1,3-bis(aminomethyl)benzene, N-2-ethylhexyl-1,3-bis-(aminomethyl)benzene, N,N'-bis(2-ethylhexyl)-1,3-bis(aminomethyl)benzene, or partially styrenized polyamines such as, for example, styrenized MXDA (available as Gaskamine® 240 from Mitsubishi Gas Chemical);

aromatic polyamines, such as, in particular, m- and p-phenylenediamine, 4,4'-, 2,4' and/or 2,2'-diaminodiphenylmethane, 3,3'-dichloro-4,4'-diaminodiphenylmethane (MOCA), 2,4- and/or 2,6-tolylenediamine, mixtures of 3,5-dimethylthio-2,4- and -2,6-tolylenediamine (available as Ethacure® 300 from Albermarle), mixtures of 3,5-diethyl-2,4- and -2,6-tolylenediamine (DETDA), 3,3',5,5'-tetraethyl-4,4'-diaminodiphenylmethane (M-DEA), 3,3',5,5'-tetraethyl-2,2'-dichloro-4,4'-diaminodiphenylmethane (M-CDEA), 3,3'-diisopropyl-5,5'-dimethyl-4,4'-diaminodiphenylmethane (M-MIPA), 3,3',5,5'-tetraisopropyl-4,4'-diaminodiphenylmethane (M-DIPA), 4,4'-diaminodiphenyl sulfone (DDS), 4-amino-N-(4-aminophenyl)benzenesulfonamide, 5,5'-methylenedianthranilic acid, dimethyl 5,5'-methylenedianthranilate, 1,3-propylene bis(4-aminobenzoate), 1,4-butylene bis(4-aminobenzoate), polytetramethylene oxide bis(4-aminobenzoate) (available as Versalink® from Air Products), 1,2-bis(2-aminophenylthio)ethane, 2-methylpropyl 4-chloro-3,5-diaminobenzoate or tert-butyl (4-chloro-3,5-diaminobenzoate);

adducts of the stated polyamines with epoxides or epoxy resins, especially adducts with diepoxides having a molar ratio of approximately 2/1, adducts with monoepoxides having a molar ratio of approximately 1/1, or reaction products of amines and epichlorohydrin, more particularly that of 1,3-bis(aminomethyl)benzene, available commercially as Gaskamine® 328 (from Mitsubishi Gas Chemical);

polyamidoamines, especially reaction products of a mono- or polybasic carboxylic acid, and/or the esters or anhydrides thereof, particularly of a dimer fatty acid, with an aliphatic, cycloaliphatic or aromatic polyamine that is used in a stoichiometric excess, more particularly a polyalkyleneamine such as, for example, DETA or TETA, more particularly the commercially available polyamidoamines Versamid® 100, 125, 140 or 150 (from Cognis), Aradur® 223, 250 or 848 (from Huntsman), Euretek® 3607 or 530 (from Huntsman) or Beckopox® EH 651, EH 654, EH 655, EH 661 or EH 663 (from Cytec); or phenalkamines, also called Mannich bases, especially reaction products of a Mannich reaction of phenols, more particularly cardanol, with aldehydes, more particularly formaldehyde, especially the commercially available phenalkamines Cardolite® NC-541, NC-557, NC-558, NC-566, Lite 2001, Lite 2002, NX-4943, NX-5607 or NX-5608 (from Cardolite), Aradur® 3440, 3441, 3442 or 3460 (from Huntsman) or Beckopox® EH 614, EH 621, EH 624, EH 628 or EH 629 (from Cytec).

Preferred as further amine are reaction products from the reductive alkylation of 1,2-propylenediamine with an aldehyde or ketone of the formula (II), wherein the $N^2$ nitrogen atom is alkylated, especially $N^2$-benzyl-1,2-propanediamine. An amine of this kind is present in particular as a constituent of a reaction product comprising the corresponding $N^1$-alkylated amine.

Additionally preferred as further amine are an adduct of (i) at least one polyamine, having at least three amine hydrogens reactive toward epoxide groups, with (ii) at least one epoxide.

Preferred as polyamine for such an adduct are the aforementioned polyamines having at least three amine hydrogens that are reactive toward epoxide groups, or smaller polyamines such as, in particular, ethylenediamine, the isomeric propylenediamines or the isomeric butylenediamines.

Preferred as epoxide for such an adduct are diepoxides, such as, in particular, bisphenol A or F or A/F diglycidyl ether, poly-1,2-propylene oxide diglycidyl ether or monoepoxides. Particularly preferred are aromatic monoepoxides, especially cresyl glycidyl ether, tert-butylphenyl glycidyl ether or the glycidyl ether of cardanol. Particularly preferred is cresyl glycidyl ether. Suitable cresyl glycidyl ethers are all isomeric cresyl glycidyl ethers or mixtures thereof, more particularly commercially available types such as, in particular, Araldite® DY-K (from Huntsman), Polypox™ R6 (from Dow), Heloxy™ KR (from Hexion) or Erisys® GE-10 (from CVC Spec. Chem.).

The adduct is prepared preferably by slow metered addition of the epoxide to an initial charge of polyamine, the temperature of the reactants being maintained preferably in the range from 40 to 120° C., more particularly 50 to 110° C.

Such adducts exhibit excellent properties as hardeners for epoxy resins, more particularly a rapid cure rate even at low temperatures and a relatively unpronounced tendency toward blushing effects. They produce films of excellent quality, but in view of their viscosity are suitable for coating applications only if they are diluted. Through the combination with an amine of the formula (I), the adduct is diluted to such an extent as to enable access to hardeners for low emission epoxy resin coatings having outstanding properties.

Preferred adducts are those of (i) at least one polyamine, having at least three amine hydrogens reactive toward epoxide groups, with (ii) at least one aromatic monoepoxide, these reactants being reacted in a molar ratio of approximately 1/1. During the reaction, the polyamine may have been present in excess and may have been removed by distillation after the reaction.

For an adduct of this kind, the polyamine is preferably selected from the group consisting of ethylenediamine, 1,2-propylenediamine, 1,3-propylenediamine, 1,4-butylenediamine, 1,3-butylenediamine, 1,2-butylenediamine, 2,3-butylenediamine, 2-methyl-1,3-propanediamine, DAMP, 2,2-dimethyl-1,3-propanediamine, 1,5-pentanediamine, MPMD, 1,6-hexanediamine, 2,5-dimethyl-1,6-hexanediamine, TMD, 1,2-diaminocyclohexane, 1,3-diaminocyclohexane, 1,4-diaminocyclohexane, IPDA, 2-methyl-1,3-diaminocyclohexane and 4-methyl-1,3-diaminocyclohexane, and mixtures thereof, 1,3-bis(aminomethyl)cyclohexane, 1,4-bis(aminomethyl)cyclohexane, 1,3-bis(aminomethyl)benzene, bis(2-aminoethyl) ether, 3,6-dioxaoctane-1,8-diamine, DETA, TETA, DPTA, N3-amine, N4-amine and BHMT.

For an adduct of this kind the aromatic monoepoxide is preferably a cresyl glycidyl ether.

Particularly preferred is an adduct of 1,2-propylenediamine with cresyl glycidyl ether that is prepared with an excess of 1,2-propylenediamine and with subsequent removal of the excess by distillation.

Further particularly preferred is an adduct of 1,5-diamino-2-methylpentane with cresyl glycidyl ether that has either been prepared with an excess of 1,5-diamino-2-methylpentane, with subsequent removal of the excess by distillation, or with a slight excess of cresyl glycidyl ether.

Further particularly preferred is an adduct of 2,2(4),4-trimethylhexamethylenediamine with cresyl glycidyl ether that is prepared with a slight excess of 2,2(4),4-trimethylhexamethylenediamine.

The term "excess" in the case of these particularly preferred adducts relates not to the reactive groups but rather to the molar ratio between the polyamine molecule and the cresyl glycidyl ether.

These particularly preferred adducts are of comparatively low viscosity, exhibit particularly high compatibility and reactivity with the customary epoxy resin compositions, have virtually no tendency toward blushing effects, and enable fully cured films of high gloss and high hardness to be produced. Without a diluent addition, however, these adducts are also of too high viscosity as hardeners for epoxy resin coatings.

Preferred as further amine, moreover, are ether group-containing aliphatic primary di- or triamines, more particularly polyoxyalkylene di- or -triamines having an average molecular weight in the range from 200 to 500 g/mol, especially Jeffamine® D-230 or Jeffamine® T-403 (both from Huntsman), or cycloaliphatic ether group-containing diamines from the propoxylation and subsequent amination of 1,4-dimethylolcyclohexane, especially Jeffamine® RFD-270 (from Huntsman). An amine of this kind allows access to epoxy resin compositions with a reliable curing to high ultimate hardness without so-called "freezing" and with low brittleness after curing. "Freezing" refers to the phenomenon whereby, after initially good development of hardness, an epoxy resin composition fails to cure to the anticipated ultimate hardness at a given temperature, the curing instead remaining at a relatively low hardness. Such effects occur in particular at low curing temperatures.

The hardener of the invention comprises preferably 1 to 95 weight %, preferably 2 to 80 weight %, more preferably 5 to 60 weight %, more particularly 5 to 40 weight %, of amine of the formula (I). Hardeners of this kind are notable for low viscosity and allow access to epoxy resin coatings having high cure rate, hardly any tendency toward blushing effects, and high hardness.

The hardener typically comprises a certain fraction of products alkylated on the $N^2$ nitrogen—in the case of $N^1$-benzyl-1,2-propanediamine, for example, a certain fraction of $N^2$-benzyl-1,2-propanediamine.

One particularly preferred hardener for epoxy resins comprises
- at least one amine of the formula (I),
- at least one adduct of (i) at least one polyamine, having at least three amine hydrogens reactive toward epoxide groups, and (ii) at least one aromatic monoepoxide, and
- at least one ether group-containing aliphatic primary di- or triamine.

The amine of the formula (I), the adduct, and the ether group-containing di- or triamine here are present more particularly in an amount such that of the total amine hydrogens in the hardener,
- 10 to 40% originate from amine of the formula (I),
- 15 to 75% from the adduct, and
- 15 to 60% from the ether group-containing di- or triamine.

A hardener of this kind has a low viscosity and cures rapidly and largely without blushing effects to form fully cured films of high gloss and high hardness with virtually no yellowing.

Another particularly preferred hardener for epoxy resins comprises
- at least one amine of the formula (I),
- at least one adduct of (i) at least one polyamine, having at least three amine hydrogens reactive toward epoxide groups, and (ii) at least one aromatic monoepoxide, and optionally at least one further amine.

The amine of the formula (I), the adduct, and the further amine here are present in an amount such that of the total amine hydrogens in the hardener,
- 10 to 80% originate from the amine of the formula (I),
- 20 to 80% from the adduct, and
- 0 to 40% from at least one further amine.

A hardener of this kind has a low viscosity and cures particularly rapidly and largely without blushing effects to form fully cured films of high gloss and high hardness with virtually no yellowing.

The hardener is preferably largely free of 1,2-propylenediamine. More particularly it contains less than 1 weight %, more preferably less than 0.1 weight %, of 1,2-propylenediamine.

With further preference the hardener is largely free from amines having a molecular weight below 120 g/mol, more particularly below 150 g/mol. The hardener contains preferably less than 2 weight %, more particularly less than 1 weight %, of amines having a molecular weight below 120 g/mol, more particularly below 150 g/mol.

A hardener of this kind has particularly toxicological and odor advantages and enables access to coatings having particularly attractive surfaces.

The hardener may further comprise at least one unincorporable diluent, more particularly xylene, 2-methoxyethanol, dimethoxyethanol, 2-ethoxyethanol, 2-propoxyethanol, 2-isopropoxyethanol, 2-butoxyethanol, 2-phenoxyethanol, 2-benzyloxyethanol, benzyl alcohol, ethylene glycol, ethylene glycol dimethyl ether, ethylene glycol diethyl ether, ethylene glycol dibutyl ether, ethylene glycol diphenyl ether, diethylene glycol, diethylene glycol monomethyl ether, diethylene glycol monoethyl ether, diethylene glycol mono-n-butyl ether, diethylene glycol dimethyl ether, diethylene glycol diethyl ether, diethylene glycol di-n-butylyl ether, propylene glycol butyl ether, propylene glycol phenyl ether, dipropylene glycol, dipropylene glycol monomethyl ether, dipropylene glycol dimethyl ether, dipropylene glycol di-n-butyl ether, N-methylpyrrolidone, diphenylmethane, diisopropylnaphthalene, petroleum fractions such as, for example, Solvesso® grades (from Exxon), alkylphenols such as tert-butylphenol, nonylphenol, dodecylphenol and 8,11,14-pentadecatrienylphenol (Cardanol, from cashew shell oil, available for example as Cardolite NC-700 from Cardolite Corp., USA), styrenized phenol, bisphenols, aromatic hydrocarbon resins, especially those containing phenol groups, alkoxylated phenol, especially ethoxylated or propoxylated phenol, more particularly 2-phenoxyethanol, adipates, sebacates, phthalates, benzoates, organic phosphoric acid esters or sulfonic acid esters or sulfonamides. Preferred are benzyl alcohol, dodecylphenol, tert-butylphenol, styrenized phenol, ethoxylated phenol, or aromatic hydrocarbon resins containing phenol groups, more particularly the Novares® grades LS 500, LX 200, LA 300 or LA 700 (from Rütgers).

The hardener preferably contains none or only a low level of unincorporable diluents. With preference the hardener contains not more than 5 weight % of unincorporable diluents.

The hardener may comprise further substances that are reactive toward epoxide groups, examples being monoamines such as hexylamine or benzylamine, or compounds containing mercapto groups, more particularly the following:
- liquid, mercaptan-terminated polysulfide polymers, known under the brand name Thiokol® (from Morton Thiokol; available for example from SPI Supplies, or from Toray Fine Chemicals), more particularly types LP-3, LP-33, LP-980, LP-23, LP-55, LP-56, LP-12, LP-31, LP-32 or LP-2; and also, moreover, under the brand name Thioplast® (from Akzo Nobel), more particularly the types G 10, G 112, G 131, G 1, G 12, G 21, G 22, G 44 or G 4;
- mercaptan-terminated polyoxyalkylene ethers, available for example by reaction of polyoxyalkylenediols or -triols either with epichlorohydrin or with an alkylene oxide, followed by sodium hydrogensulfide;

mercaptan-terminated compounds in the form of polyoxyalkylene derivatives known under the brand name Capcure® (from Cognis), especially types WR-8, LOF or 3-800;

polyesters of thiocarboxylic acids, for example pentaerythritol tetramercaptoacetate, trimethylolpropane trim ercaptoacetate, glycol di mercaptoacetate, pentaerythritol tetra(3-mercaptopropionate), trimethylolpropane tri(3-mercaptopropionate) or glycol di-(3-mercaptopropionate), or products of esterification of polyoxyalkylenediols or -triols, of ethoxylated trimethylolpropane or of polyester diols with thiocarboxylic acids such as thioglycolic acid or 2- or 3-mercaptopropionic acid; or further compounds containing mercapto groups, such as, in particular, 2,4,6-trimercapto-1,3,5-triazine, 2,2'-(ethylenedioxy)diethanethiol (triethylene glycol dimercaptan) or ethanedithiol.

A further subject of the invention is an epoxy resin composition comprising a resin component comprising at least one epoxy resin and
a hardener component comprising at least one amine of the formula (I) as described above.

The hardener component preferably comprises a hardener comprising at least one amine of the formula (I) and at least one further amine and/or at least one accelerator, as described above.

Suitability as epoxy resin is possessed by customary technical epoxy resins. These are obtained in a known manner, as for example from the oxidation of the corresponding olefins or from the reaction of epichlorohydrin with the corresponding polyols, polyphenols or amines.

Particularly suitable as epoxy resin are what are called liquid polyepoxy resins, referred to hereinafter as "liquid resin". These have a glass transition temperature below 25° C.

Likewise possible as epoxy resin are what are called solid resins, which have a glass transition temperature above 25° C. and can be comminuted to powders which are pourable at 25° C.

Suitable epoxy resins are, in particular, aromatic epoxy resins, more particularly the glycidylization products of:

bisphenol A, bisphenol F or bisphenol A/F, where A stands for acetone and F for formaldehyde, which served as reactants in the preparation of these bisphenols. In the case of bisphenol F, there may also be positional isomers present, derived more particularly from 2,4'- or 2,2'-hydroxyphenylmethane.

dihydroxybenzene derivatives such as resorcinol, hydroquinone or pyrochatechol;

further bisphenols or polyphenols such as bis(4-hydroxy-3-methylphenyl)methane, 2,2-bis(4-hydroxy-3-methylphenyl)propane (bisphenol C), bis-(3,5-dimethyl-4-hydroxyphenyl)methane, 2,2-bis(3,5-dimethyl-4-hydroxyphenyl)propane, 2,2-bis(3,5-dibromo-4-hydroxyphenyl)propane, 2,2-bis(4-hydroxy-3-tert-butylphenyl)propane, 2,2-bis(4-hydroxyphenyl)butane (bisphenol B), 3,3-bis(4-hydroxyphenyl)pentane, 3,4-bis(4-hydroxyphenyl)hexane, 4,4-bis(4-hydroxyphenyl)heptane, 2,4-bis(4-hydroxyphenyl)-2-methylbutane, 2,4-bis(3,5-dimethyl-4-hydroxyphenyl)-2-methylbutane, 1,1-bis(4-hydroxyphenyl)cyclohexane (bisphenol Z), 1,1-bis(4-hydroxyphenyl)-3,3,5-trimethylcyclohexane (bisphenol-TMC), 1,1-bis(4-hydroxyphenyl)-1-phenylethane, 1,4-bis[2-(4-hydroxyphenyl)-2-propyl]benzene (bisphenol P), 1,3-bis[2-(4-hydroxyphenyl)-2-propyl]benzene (bisphenol M), 4,4'-dihydroxybiphenyl (DOD), 4,4'-dihydroxybenzophenone, bis(2-hydroxynaphth-1-yl) methane, bis(4-hydroxynaphth-1-yl)methane, 1,5-dihydroxynaphthalene, tris(4-hydroxyphenyl)methane, 1,1,2,2-tetrakis(4-hydroxyphenyl)ethane, bis(4-hydroxyphenyl) ether or bis(4-hydroxyphenyl) sulfone;

condensation products of phenols with formaldehyde which are obtained under acidic conditions, such as phenol novolaks or cresol novolaks, also called bisphenol F novolaks;

aromatic amines, such as aniline, toluidine, 4-aminophenol, 4,4'-methylenediphenyldiamine, 4,4'-methylenediphenyldi-(N-methyl)amine, 4,4'-[1,4-phenylenebis(1-methylethylidene)]bisaniline (bisaniline P) or 4,4'-[1,3-phenylenebis(1-methylethylidene)]bisaniline (bisaniline M).

Further suitable epoxy resins are aliphatic or cycloaliphatic polyepoxides, more particularly glycidyl ethers of saturated or unsaturated, branched or unbranched, cyclic or open-chain di-, tri- or tetrafunctional $C_2$ to $C_{30}$ alcohols, especially ethylene glycol, propylene glycol, butylene glycol, hexanediol, octanediol, polypropylene glycols, dimethylolcyclohexane, neopentyl glycol, dibromoneopentyl glycol, castor oil, trimethylolpropane, trimethylolethane, pentaerythritol, sorbitol or glycerol, or alkoxylated glycerol or alkoxylated trimethylolpropane;

a hydrogenated bisphenol A, F or A/F liquid resin, or the glycidylation products of hydrogenated bisphenol A, F or A/F;

a N-glycidyl derivative of amides or heterocyclic nitrogen bases, such as triglycidyl cyanurate or triglycidyl isocyanurate, or reaction products of epichlorohydrin with hydantoin.

epoxy resins from the oxidation of olefins, such as, in particular, vinylcyclohexene, dicyclopentadiene, cyclohexadiene, cyclododecadiene, cyclododecatriene isoprene, 1,5-hexadiene, butadiene, polybutadiene or divinylbenzene.

A preferred epoxy resin in the resin component is a liquid resin based on a bisphenol, more particularly a diglycidyl ether of bisphenol A, bisphenol F or bisphenol A/F, of the kind available commercially, for example, from Dow, Huntsman or Momentive. These liquid resins have a low viscosity for epoxy resins and in the cured state exhibit good properties as a coating. They may include fractions of solid bisphenol A resin or bisphenol F novolaks.

The resin component may comprise are active diluent, more particularly a reactive diluent having at least one epoxide group. Particularly suitable as reactive diluents are the glycidyl ethers of mono- or polyhydric phenols or aliphatic or cycloaliphatic alcohols, such as, in particular, the aforementioned polyglycidyl ethers of di- or polyols, or, furthermore, phenyl glycidyl ether, cresyl glycidyl ether, benzyl glycidyl ether, p-n-butylphenyl glycidyl ether, p-tert-butylphenyl glycidyl ether, nonylphenyl glycidyl ether, allyl glycidyl ether, butyl glycidyl ether, hexyl glycidyl ether, 2-ethylhexyl glycidyl ether, or glycidyl ethers of natural alcohols such as, in particular, $C_8$ to $C_{10}$ alkyl glycidyl ether or $C_{12}$ to $C_{14}$ alkyl glycidyl ether. The addition of a reactive diluent to the epoxy resin has the effect of reducing the viscosity, and/or of reducing the glass transition temperature and/or the mechanical values.

The epoxy resin composition optionally comprises further constituents, particularly auxiliaries and adjuvants customarily used in epoxy resin compositions, examples being the following:

solvents, diluents, film-forming assistants or extenders, such as especially the aforementioned unincorporable diluents;

reactive diluents, especially reactive diluents containing epoxide groups, as mentioned above, epoxidized soybean oil or linseed oil, compounds containing acetoacetate groups, especially acetoacetylated polyols, butyrolactone, carbonates, aldehydes, and also, moreover, isocyanates or silicones containing reactive groups;

polymers, especially polyamides, polysulfides, polyvinylformal (PVF), polyvinylbutyral (PVB), polyurethanes (PU), polymers with carboxyl groups, polyamides, butadiene-acrylonitrile copolymers, styrene-acrylonitrile copolymers, butadiene-styrene copolymers, homo- or copolymers of unsaturated monomers, especially from the group encompassing ethylene, propylene, butylene, isobutylene, isoprene, vinyl acetate or alkyl (meth)acrylates, especially chlorosulfonated polyethylenes or fluorine-containing polymers, sulfonamide-modified melamines or purified Montan waxes;

inorganic or organic fillers, especially ground or precipitated calcium carbonates, with or without a coating of fatty acids, more particularly of stearates, barytes (heavy spar), talcs, finely ground quartzes, silica sand, iron mica, dolomites, wollastonites, kaolins, mica (potassium aluminum silicate), molecular sieves, aluminum oxides, aluminum hydroxides, magnesium hydroxide, silicas, cements, gypsums, flyashes, carbon black, graphite, metal powders such as aluminum, copper, iron, zinc, silver or steel, PVC powders or hollow beads;

fibers, especially glass fibers, carbon fibers, metal fibers, ceramic fibers, or polymeric fibers such as polyamide fibers or polyethylene fibers;

pigments, especially titanium dioxide and/or iron oxides;

the aforementioned accelerators;

rheology modifiers, especially thickeners or antisettling agents;

adhesion promoters, especially organoalkoxysilanes;

stabilizers against oxidation, heat, light or UV radiation;

flame retardants, especially aluminum hydroxide (ATH), magnesium dihydroxide (MDH), antimony trioxide, antimony pentoxide, boric acid $(B(OH)_3)$, zinc borate, zinc phosphate, melamine borate, melamine cyanurate, ammonium polyphosphate, melamine phosphate, melamine pyrophosphate, polybrominated diphenyl oxides or diphenyl ethers, phosphates such as especially diphenyl cresyl phosphate, resorcinol bis(diphenyl phosphate), resorcinol diphosphate oligomer, tetraphenylresorcinol diphosphite, ethylenediamine diphosphate or bisphenol A bis(diphenyl phosphate), tris(chloroethyl) phosphate, tris(chloro-propyl) phosphate or tris(dichloroisopropyl) phosphate, tris[3-bromo-2,2-bis-(bromomethyl)propyl]phosphate, tetrabromobisphenol A, bis(2,3-dibromopropyl ether) of bisphenol A, brominated epoxy resins, ethylenebis(tetrabromophthalimide), ethylenebis(dibromonorbornanedicarboximide), 1,2-bis(tribromophenoxy)ethane, tris(2,3-dibromopropyl) isocyanurate, tribromophenol, hexabromocyclododecane, bis(hexachlorocyclopentadieno)cyclooctane or chlorinated paraffins;

surface-active substances, especially wetting agents, flow control agents, deaerating agents or defoamers;

biocides, such as, for example, algicides, fungicides or fungal growth inhibitors.

The epoxy resin composition preferably comprises further auxiliaries and adjuvants, especially wetting agents, flow control agents, defoamers, stabilizers, pigments and/or accelerators, especially salicylic acid and/or 2,4,6-tris(dimethylaminomethyl)phenol.

The epoxy resin composition preferably contains none or only a small amount of unincorporable diluents, preferably not more than 5 weight %, especially not more than 2 weight %.

The ratio of the number of groups that are reactive toward epoxide groups in the epoxy resin composition, to the number of epoxide groups, is preferably in the range from 0.5 to 1.5, more particularly 0.7 to 1.2.

The amine hydrogens and, where present, other groups that are reactive toward epoxide groups, present in the epoxy resin composition, react with the epoxide groups with ring-opening of the latter groups (addition reaction). As a result of these reactions, the composition undergoes polymerization and ultimately cures. The person skilled in the art is aware that primary amino groups are difunctional groups with respect to epoxide groups, and a primary amino group therefore counts as two groups that are reactive toward epoxide groups.

The two components of the epoxy resin composition are each stored in their own container. Further constituents of the epoxy resin composition may be present as part of the resin component or of the hardener component, with further constituents that are reactive toward epoxide groups preferably being part of the hardener component. A suitable container for storing the resin component or the hardener component is, in particular, a drum, a Hobbock, a pouch, a pail, a canister, a cartridge or a tube. The components are storable, meaning that they can be kept for several months up to a year or more before being employed, without suffering alteration in their respective properties to any extent relevant for their use. For the use of the epoxy resin composition, the resin component and the hardener component are mixed with one another shortly before or during application. The mixing ratio between the two components is preferably selected such that the groups of the hardener component that are reactive toward epoxide groups are present in an appropriate ratio to the epoxide groups of the resin component, as described above. In terms of parts by weight, the mixing ratio between the resin component and the hardener component is customarily in the range from 1:10 to 10:1.

The two components are mixed by means of suitable method; this may take place continuously or batchwise. If mixing takes place prior to application, it should be ensured that not too much time elapses between the mixing of the components and application, since otherwise there may be disruptions, such as retarded or incomplete development of adhesion to the substrate, for example. Mixing takes place in particular at ambient temperature, which is typically in the range from about 5 to 50° C., preferably at about 10 to 30° C. The mixing of the two components is at the same time the start of curing through chemical reaction, as described above. Curing takes place in particular at ambient temperature. It typically extends over several days to weeks, until it has largely concluded under the prevailing conditions. The duration is dependent on factors including the temperature, the reactivity of the constituents and their stoichiometry, and also the presence of accelerators. A further subject of the invention, accordingly, is also a cured composition obtained from the curing of an epoxy resin composition as described in the present document.

The epoxy resin composition is applied to at least one substrate, those below being particularly suitable:

glass, glass-ceramic, concrete, mortar, brick, tile, plaster or natural stones such as granite or marble;

metals or alloys such as aluminum, iron, steel or nonferrous metals, or surface-enhanced metals or alloys such as galvanized or chromed metals;

leather, textiles, paper, wood, woodbase materials bonded with resins, such as phenolic, melamine or epoxy resins, for example, resin-textile composites, or other polymer composites;

plastics, especially rigid or flexible PVC, ABS, polycarbonate (PC), polyamide (PA), polyesters, PMMA, epoxy resins, PU, POM, PO, PE, PP, EPM or EPDM, the plastics having optionally been surface-treated by plasma, corona or flame treatment;

fiber-reinforced plastics, such as carbon fiber-reinforced plastics (CRP), glass fiber-reinforced plastics (GRP) or sheet molding compounds (SMC);

coated substrates, such as powder-coated metals or alloys; paints or varnishes.

As and when necessary, the substrates may be pretreated before the epoxy resin composition is applied. Such pretreatments include, in particular, physical and/or chemical cleaning techniques, as for example sanding, sandblasting, shotblasting, brushing and/or blowing, and also, furthermore, treatment with cleaners or solvents, or the application of an adhesion promoter, an adhesion promoter solution or a primer.

The epoxy resin composition described can be used with advantage as a fiber composite matrix for fiber composite materials (composites) such as, in particular, CRP or GRP, or as an encapsulating compound, sealant, adhesive, covering, coating, paint, varnish, seal, priming coat or primer.

More particularly it can be used as an encapsulating compound, such as an electrical encapsulant, for example, or as an adhesive, more particularly as a bodywork adhesive, sandwich element adhesive, half-shell adhesive for rotor blades of wind turbines, bridge element adhesive or anchoring adhesive.

It can also be used, in particular, as a covering, coating, paint, varnish, seal, priming coat for primer for construction and industry applications, more particularly as a floor covering or floor coating for interiors such as offices, industrial halls, sports halls or cooling rooms, or, in the exterior segment, for balconies, terraces, parking decks, bridges or roofs, as a protective coating for concrete, cement, metals, plastics or wood, for the surface sealing of wooden constructions, vehicles, loading areas, tanks, silos, shafts, piping circuits, pipelines, machines or steel constructions, for example, such as of boats, piers, offshore platforms, sluice gates, hydroelectric power stations, river constructions, swimming pools, wind turbines, bridges, chimneys, cranes or sheet-pile walls, for example.

In particular, moreover, it can be used as an undercoat, tie coat, anticorrosion primer, or for rendering surfaces hydrophobic.

The fully or partly cured epoxy resin composition, especially when used as a coating, covering or paint, may have a further coating, covering or paint applied to it, in which case this further layer may likewise comprise an epoxy resin composition, or else may comprise a different material, particularly a polyurethane coating or polyurea coating.

With particular advantage the epoxy resin composition described is used as a coating.

A further subject of the invention, accordingly, is a coating comprising an epoxy resin composition as described above.

A coating in this context refers to two-dimensionally applied coverings of all kinds, especially paints, varnishes, seals, priming coats or primers, as described above, or floor coverings or protective coatings, including in particular those for heavy-duty corrosion control. With particular advantage the epoxy resin composition described is used in low-emission coatings that carry eco-quality seals, according for example to Emicode (EC1 Plus), AgBB, DIBt, Der Blaue Engel, AFSSET, RTS (M1), and US Green Building Council (LEED).

As a coating, the epoxy resin composition is used advantageously in a method for coating, where it has a liquid consistency with low viscosity and good leveling properties and is applied more particularly as a self-leveling or thixotrope coating to predominantly planar surfaces or as a paint. In the context of this application, the viscosity of the epoxy resin composition immediately after the mixing of the resin and hardener components, and as measured at 20° C., is preferably in the range from 300 to 4000 mPa·s, preferably in the range from 300 to 2000 mPa·s, more preferably in the range from 300 to 1500 mPa·s. Within the working time, the mixed composition is applied two-dimensionally as a thin film having a layer thickness of typically about 50 μm to about 5 mm to a substrate, typically at ambient temperature. Application is accomplished in particular by pouring the composition onto the substrate that is to be coated, and then spreading it evenly with the aid, for example, of a doctor blade or toothed applicator. Application may alternatively take place with a brush or roller or by spray application, as an anticorrosion coating on steel, for example.

Curing is typically accompanied by the development of largely clear, glossy and nonsticky films of high-hardness, which exhibit effective adhesion to a very wide variety of substrates.

The use of the epoxy resin composition results in an article comprising the cured composition from the curing of the epoxy resin composition described. The cured composition here is present in particular in the form of a coating.

The epoxy resin composition described is notable for advantageous properties. It is of very low viscosity and odor and cures rapidly, even under damp and cold conditions, and does so largely without blushing effects, even when the fractions of unincorporable diluents are small or none are used at all, and in particular also without the use of volatile, intensely odorous amines. In two-dimensional use as a coating, the resulting films are clear, nonsticky, very hard, and of high surface quality, with virtually no yellowing under the influence of light. Accessible in particular with the epoxy resin composition described are low-emission epoxy resin products which fulfill the conditions for numerous eco-quality seals and at the same time satisfy exacting requirements in terms of operational safety, processing properties and service properties.

A further subject of the invention is a method for the dilution of a hardener for epoxy resins and/or of an epoxy resin, by addition of an amine of the formula (I) as described above. The hardener for epoxy resins here comprises in particular an adduct or a polyamidoamine or a Mannich base, as described above. The epoxy resin here represents an epoxy resin as described above.

EXAMPLES

Set out below are working examples which are intended to elucidate in more detail the invention described. The invention is of course not confined to these working examples described.

"ANEW" stands for the amine hydrogen equivalent weight.

"EEW" stands for the epoxide equivalent weight.

"Standard conditions" refer to a temperature of 23±1° C. and a relative atmospheric humidity of 50±5%. "SC" stands for "standard conditions".

Description of Measurement Methods:

Infrared spectra (FT-IR) were measured as undiluted films on an FT-IR instrument 1600 from Perkin-Elmer equipped with a horizontal ATR measurement unit with ZnSe crystal; the absorption bands are reported in wavenumbers (cm$^{-1}$); (measuring window: 4000-650 cm$^{-1}$).

$^1$H-NMR spectra were measured on a Bruker Ascend 400 spectrometer at 400.14 MHz; the chemical shifts δ are reported in ppm relative to tetramethylsilane (TMS). No distinction is made between true and pseudo-coupling patterns.

Gas chromatograms (GC) were measured in the temperature range from 60 to 320° C. at a heating rate of 15° C./min and 10 min dwell time at 320° C. The injector temperature was 250° C. A Zebron ZB-5 column was used (L=30 m, ID=0.25 mm, dj=0.5 μm) with a gas flow rate of 1.5 ml/min. Detection took place by means of flame ionization (FID).

The viscosity of samples with relatively high viscosity (above 150 mPa·s) was measured on a thermostated cone/plate viscometer, Rheotec RC30 (cone diameter 50 mm, cone angle 1°, cone tip/plate distance 0.05 mm, shear rate 10 s$^{-1}$).

The viscosity of low-viscosity samples (below 150 mPa·s) was measured on a thermostated cone/plate rheometer, Anton Paar Physica MCR 300 (cone diameter 25 mm, cone angle 2°, cone tip/plate distance 0.05 mm, shear rate 100 s$^{-1}$).

The amine number was determined by titration (with 0.1N HClO$_4$ in acetic acid against crystal violet).

Substances Used:

| | |
|---|---|
| Araldite ® GY 250: | bisphenol A diglycidyl ether, EEW about 187.5 g/eq (from Huntsman) |
| Araldite ® DY-E: | monoglycidyl ether of C$_{12}$ to C$_{14}$ alcohols, EEW about 290 g/eq (from Huntsman) |
| Ancamine ® K54: | 2,4,6-tris(dimethylaminomethyl)phenol (from Air Products) |
| Araldite ® DY-K: | cresyl glycidyl ether, EEW about 182 g/eq (from Huntsman) |
| EP adduct 1: | reaction product of 1,5-diamino-2-methylpentane and Araldite ® DY-K, as described below; AHEW about 109.5 g/eq; viscosity (20° C.) 13 100 mPa · s |
| EP adduct 2: | reaction product of 1,5-diamino-2-methylpentane and Araldite ® DY-K, as described below; AHEW about 106.5 g/eq; viscosity (20° C.) 13 000 mPa · s |
| EP adduct 3: | reaction product of 1,2-propylenediamine and Araldite ® DY-K, as described below; AHEW about 90.0 g/eq; viscosity (20° C.) 23 000 mPa · s |
| Jeffamine ® D-230: | polyoxypropylenediamine with average molecular weight of about 240 g/mol, AHEW about 60 g/eq (from Huntsman) |
| Gaskamine ® 240: | styrenized 1,3-bis(aminomethyl)benzene; AHEW 103 g/eq; viscosity (20° C.) 165 mPa · s (from Mitsubishi Gas Chemical) |
| 1,3-bis(benzylaminomethyl)benzene: | prepared as N,N'-dibenzyl-m-xylylenediamine (amine 1) in WO 2013/010842 |

EP adduct 1 was prepared by initially introducing 116.0 g of 1,5-diamino-2-methylpentane (Dytek® A from Invista) under a nitrogen atmosphere, heating this initial charge to 70° C. and then slowly adding 200.2 g of Araldite® DY-K with thorough stirring, the temperature of the reaction mixture being 70 to 80° C. After 1 hour at 80° C., the reaction mixture was cooled.

EP adduct 2 was prepared by initially introducing 4.65 kg of 1,5-diamino-2-methylpentane (Dytek® A from Invista) under a nitrogen atmosphere, heating this initial charge to 70° C. and then slowly adding 1.83 kg of Araldite® DY-K with thorough stirring, the temperature of the reaction mixture being 70 to 80° C. After 1 hour at 80° C., the reaction mixture was cooled and the volatile constituents were removed by distillation using a thin-film evaporator (0.5-1 mbar, jacket temperature 160° C.).

EP adduct 3 was prepared by initially introducing 4.15 kg of 1,2-propylenediamine under a nitrogen atmosphere, heating this initial charge to 70° C. and then slowly adding 2.93 kg of Araldite® DY-K with thorough stirring, the temperature of the reaction mixture being 70 to 80° C. After 1 hour at 80° C., the reaction mixture was cooled and the volatile constituents were removed by distillation using a thin-film evaporator (0.5-1 mbar, jacket temperature 115° C.).

Preparation of Amines of Formula (I)

Amine 1: Reaction Mixture Comprising N$^1$-benzyl-1,2-propanediamine

A round-bottomed flask was charged at room temperature with 22.1 g (0.3 mol) of 1,2-propanediamine under a nitrogen atmosphere. With thorough stirring, a solution of 31.8 g (0.3 mol) of benzaldehyde in 500 ml of isopropanol was added slowly dropwise, followed by stirring for 30 minutes more. Thereafter the reaction mixture was hydrogenated under a hydrogen pressure of 85 bar, at a temperature of 85° C. and with a flow rate of 5 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated under reduced pressure at 65° C. This gave a clear, slightly yellowish liquid having a viscosity of 19 mPa·s at 20° C. and an amine number of 573.7 mg KOH/g.

FT-IR: 3026, 2956, 2818, 1601, 1494, 1452, 1373, 1115, 1073, 1028, 826, 732, 696.

Amine 1A: Reaction Mixture Comprising N$^1$-benzyl-1,2-propanediamine

A round-bottomed flask was charged at room temperature with 444.8 g (6 mol) of 1,2-propanediamine under a nitrogen atmosphere. With thorough stirring, a solution of 212.2 g (2 mol) of benzaldehyde in 1500 ml of isopropanol was added slowly dropwise with stirring continued for 2 hours thereafter. The reaction mixture was subsequently hydrogenated under a hydrogen pressure of 90 bar at a temperature of 85° C. and with a flow rate of 5 ml/min on a continuous hydrogenation apparatus with Pd/C fixed-bed catalyst. For reaction monitoring, IR spectroscopy was used to verify whether the imine band at about 1665 cm$^{-1}$ had disappeared. At that point the hydrogenated solution was concentrated at 65° C. on a rotary evaporator, with removal of unreacted 1,2-propanediamine and isopropanol. This gave a clear, slightly yellowish liquid having an amine number of 574 mg KOH/g.

Amine 1D: Mixture of N$^1$-benzyl-1,2-propanediamine and N$^2$-benzyl-1,2-propanediamine 300 g of the amine 1A as prepared above were distilled under reduced pressure at 80° C., and 237.5 g of distillate with a vapor temperature of 60 to 63° C. at 0.08 to 0.09 bar were collected. This gave a colorless liquid having a viscosity of 8.5 mPa·s at 20° C., an amine number of 682 mg KOH/g and a purity as determined by GC of >97% (retention time 8.73-8.83 min). According to $^1$H-NMR, the ratio between $N^1$-benzyl-1,2-propanediamine and $N^2$-benzyl-1,2-propanediamine was about 2/1.

$^1$H-NMR (CDCl$_3$): 7.23-7.30 (m, 5H, Ar—H), 3.75 (m, 2H, Ar—CH$_2$), 2.9-2.5 (m, 3H, —CH$_2$—; CHCH$_3$), 1.32 (b, 3H, NH and NH$_2$), 1.03 (t, 3H, CH$_3$).

FT-IR: 3361, 3229, 3025, 2956, 2817, 1601, 1494, 1452, 1372, 1115, 1027, 824, 732.

Amine 2: Reaction Mixture Comprising N,N'-dibenzyl-1,2-propylenediamine

A round-bottomed flask was charged at room temperature with 7.4 g (0.1 mol) of 1,2-propanediamine under a nitrogen atmosphere. With thorough stirring, 17.0 g (0.16 mol) of benzaldehyde was added slowly dropwise, followed by stirring for 30 minutes, and the reaction mixture was dissolved in 300 ml of isopropanol. The solution was hydrogenated under a hydrogen pressure of 85 bar, at a temperature of 85° C. and with a flow rate of 5 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated under reduced pressure at 65° C. This gave a clear, slightly yellowish liquid having a viscosity of 41 mPa·s at 20° C. and an amine number of 492.3 mg KOH/g.

FT-IR: 3026, 2959, 2802, 1602, 1494, 1452, 1373, 1155, 1115, 1067, 1027, 824, 732, 696.

Amine 3: Reaction Mixture Comprising $N^1$-(4-dimethylaminobenzyl)-1,2-propanediamine A round-bottomed flask was charged at room temperature with 14.8 g (0.2 mol) of 1,2-propanediamine under a nitrogen atmosphere. With thorough stirring, a solution of 29.8 g (0.2 mol) of 4-dimethylaminobenzaldehyde in 450 ml of isopropanol and 50 ml of ethyl acetate was added slowly dropwise, followed by stirring for 30 minutes. Thereafter the reaction mixture was hydrogenated under a hydrogen pressure of 85 bar, at a temperature of 85° C. and with a flow rate of 5 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated under reduced pressure at 65° C. This gave a clear, slightly yellowish liquid having a viscosity of 16 mPa·s at 20° C. and an amine number of 667.4 mg KOH/g.

FT-IR: 2954, 2917, 2878, 2798, 1614, 1519, 1443, 1340, 1222, 1161, 1130, 1059, 946, 802, 685.

Amine 3D: Mixture of $N^1$-(4-dimethylaminobenzyl)-1,2-propanediamine and $N^2$-(4-dimethylaminobenzyl)-1,2-propanediamine A round-bottomed flask was charged at room temperature with 88.94 g (1.2 mol) of 1,2-propanediamine under a nitrogen atmosphere. With thorough stirring, a solution of 44.75 g (0.3 mol) of 4-dimethylaminobenzaldehyde in 800 ml of isopropanol was added slowly dropwise, with stirring continued for 2 hours thereafter. The reaction mixture was hydrogenated under a hydrogen pressure of 90 bar, at a temperature of 85° C. and with a flow rate of 5 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated on a rotary evaporator at 65° C., with removal of unreacted 1,2-propylenediamine and isopropanol. The reaction mixture thus obtained was a clear, yellowish liquid having an amine number of 667 mg KOH/g.

53 g of this reaction mixture were distilled under reduced pressure at 115° C., and 41.9 g of distillate were collected at a vapor temperature of 96 to 98° C. and at 0.02 bar. This gave a colorless liquid having a viscosity of 25 mPa·s at 20° C., an amine number of 811.5 mg KOH/g and a purity as determined by GC of >97% (retention time 12.21 min and 12.29 min), which was used hereinafter as amine 3D. According to GC, the ratio between $N^1$-(4-dimethylaminobenzyl)-1,2-propanediamine and $N^2$-(4-dimethylaminobenzyl)-1,2-propanediamine was about 4/1.

$^1$H-NMR (CDCl$_3$): 7.18 (d, 2H, Ar—H), 6.70 (d, 2H, Ar—H), 3.69 (d, 2H, Ar—CH$_2$), 2.96 and 2.65 (2×m, 3H, —CH$_2$—; CHCH$_3$), 2.92 (s, 6H, N—(CH$_3$)$_2$), 1.33 (b, 3H, NH and NH$_2$), 1.03 (t, 3H, CHCH$_3$).

FT-IR: 3299, 2954, 2798, 1613, 1564, 1505, 1442, 1341, 1221, 1161, 1128, 1059, 945, 802.

Amine 4: Reaction Mixture Comprising $N^1$-(4-methoxybenzyl)-1,2-propanediamine A round-bottomed flask was charged at room temperature with 14.8 g (0.2 mol) of 1,2-propanediamine under a nitrogen atmosphere. With thorough stirring, a solution of 27.2 g (0.2 mol) of 4-methoxybenzaldehyde (i.e. anisaldehyde) in 500 ml of isopropanol was added slowly dropwise, followed by stirring for 30 minutes. The reaction mixture was hydrogenated under a hydrogen pressure of 85 bar, at a temperature of 85° C. and with a flow rate of 5 m l/m in, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated under reduced pressure at 65° C. This gave a clear, slightly yellowish liquid having a viscosity of 39 mPa·s at 20° C. and an amine number of 501.2 mg KOH/g.

FT-IR: 2955, 2906, 2833, 1610, 1584, 1510, 1455, 1441, 1300, 1242, 1173, 1105, 1033, 811, 702.

Amine 4D: Mixture of $N^1$-(4-methoxybenzyl)-1,2-propanediamine and $N^2$-(4-methoxybenzyl)-1,2-propanediamine A round-bottomed flask was charged at room temperature with 148.3 g (2 mol) of 1,2-propanediamine under a nitrogen atmosphere. With thorough stirring, a solution of 54.4 g (0.4 mol) of 4-methoxybenzaldehyde (i.e. anisaldehyde) in 800 ml of isopropanol was added slowly dropwise, with stirring continued for 2 hours thereafter. The reaction mixture was hydrogenated under a hydrogen pressure of 90 bar, at a temperature of 90° C. and with a flow rate of 5 m l/m in, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated on a rotary evaporator at 65° C., with removal of unreacted 1,2-propylenediamine and isopropanol. The reaction mixture thus obtained was a clear, slightly yellowish liquid having an amine number of 560 mg KOH/g.

40 g of this reaction mixture were distilled under reduced pressure at 110° C., and 29.6 g of distillate were collected at a vapor temperature of 89 to 95° C. and at 0.02 bar. This gave a colorless liquid having a viscosity of 23 mPa·s at 20° C., an amine number of 575 mg KOH/g and a purity as determined by GC of >97% (retention time 10.85-10.95 min), which was used hereinafter as amine 4D.

$^1$H-NMR (CDCl$_3$): 7.22 (d, 2H, Ar—H), 6.85 (d, 2H, Ar—H), 3.78 (s, 3H, OCH$_3$), 3.71 (d, 2H, Ar—CH$_2$), 2.9-2.5 (m, 3H, —CH$_2$—; CHCH$_3$), 1.32 (b, 3H, NH and NH$_2$), 1.04 (t, 3H, CHCH$_3$).

FT-IR: 3367, 3298, 2955, 2924, 2832, 1610, 1584, 1509, 1461, 1299, 1248, 1173, 1033, 811.

Amine 5: Reaction Mixture Comprising
N-benzyl-1,3-propanediamine (Comparative)

A round-bottomed flask was charged at room temperature with 148.3 g (2 mol) of 1,3-propanediamine under a nitrogen atmosphere. With thorough stirring, a solution of 42.4 g (0.4 mol) of benzaldehyde in 800 ml of isopropanol was added slowly dropwise, followed by stirring for 2 hours more. The reaction mixture was subsequently hydrogenated under a hydrogen pressure of 90 bar, at a temperature of 90° C. and with a flow rate of 5 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated on a rotary evaporator at 65° C., with removal of unreacted 1,3-propanediamine and isopropanol. This gave a clear, slightly yellowish liquid having an amine number of 569 mg KOH/g.

Amine 5D: N-benzyl-1,3-propanediamine
(Comparative)

30 g of the amine 5 as prepared above were distilled under reduced pressure at 90° C., and 20.3 g of distillate with a vapor temperature of 68 to 73° C. at 0.06 bar were collected. This gave a colorless liquid having a viscosity of 10.8 mPa·s at 20° C., an amine number of 682 mg KOH/g and a purity as determined by GC of >97% (retention time 9.39-9.46 min).

Blushing of the Amines Prepared

Of each amine as per table 1, 1 g was placed into an open dish having a diameter of 4 cm and stored under standard conditions. For each sample, the amine was present as a clear liquid at the start. After 16 hours and after 48 hours, the appearance was assessed in each case. In addition, the increase in weight of the sample was determined after 72 hours.

TABLE 1

Blushing of amines stored open under standard conditions

| Sample | Visual assessment | | Weight increase after |
|---|---|---|---|
| | after 16 h | after 48 h | 72 h |
| Amine 1D[1] | clear liquid | clear liquid | 0.22 g |
| Amine 4D[1] | clear liquid | clear liquid | 0.19 g |
| Amine 5D[1] | white specks on the surface | white crust on the surface | 0.29 g |
| IPDA[2] | white specks on the surface | white crust on the surface | 0.33 g |
| MXDA[3] | whitish haze to surface | white crust on the surface | 0.33 g |
| D230[4] | clear liquid | clear liquid | 0.24 g |

[1]as prepared above
[2]1-amino-3-aminomethyl-3,5,5-trimethylcyclohexane
[3]1,3-bis(aminomethyl)benzene
[4]Jeffamine ® D-230

Production of Hardeners and Epoxy Resin Compositions

For each example, the ingredients specified in tables 2 to 6 were mixed in the stated quantities (in parts by weight) of the hardener component using a centrifugal mixer (Speed-Mixer™ DAC 150, FlackTek Inc.) and the mixtures were stored in the absence of moisture.

Similarly, the ingredients of the resin component as specified in tables 2 to 6 were processed and stored.

Thereafter the two components of each composition were processed to a homogeneous liquid using the centrifugal mixer, and this liquid was tested immediately as follows:

10 minutes after mixing, the viscosity at 20° C. was ascertained ("viscosity (10')").

A first film was drawn down in a film thickness of 500 μm onto a glass plate, which was stored/cured under standard conditions. Determined on this film was the König hardness (pendulum hardness as König, measured to DIN EN ISO 1522) after 1 day ("König hardness (1 d SC)"), after 2 days ("König hardness (2 d SC)"), after 4 days ("König hardness (4 d SC)"), after 7 days ("König hardness (7 d SC)"), and after 14 days ("König hardness (14 d SC)"). After 14 days, the appearance of the film was assessed (identified in the table as "appearance (SC)". A film identified as "attractive" there was clear and had a glossy and nonsticky surface without structure. "Structure" here refers to any kind of marking or pattern on the surface.

A second film was drawn down onto a glass plate in a film thickness of 500 μm, and this film immediately after application was stored, or cured, at 8° C. and at 80% relative humidity for 7 days and subsequently under standard conditions (SC) for 3 weeks. 24 hours after application, a polypropylene bottle cap was placed onto the film, with a moist sponge placed beneath the cap. After a further 24 hours, the sponge and the cap were removed and were placed on a new site on the film, where, after 24 hours, they were removed again and placed anew, a total of 4 times. Thereafter the appearance of this film was assessed (identified in the tables as "appearance (8°/80%)"), in the same way as described for the appearance (SC). Also reported here in each case is the number of marks visible in the film as a result of the wet sponge and/or the applied cap. On the films cured in this way, the König hardness was again determined, in each case after 7 days at 8° C. and 80% relative humidity ("König hardness (7 d 8°/80%)"), then after a further 2 days under SC ("König hardness (+2 d SC)"), 7 days under SC ("König hardness (+7 d SC)"), and after 14 d under SC ("König hardness (+14 d SC)") or after 3 weeks under SC ("König hardness (+3 w SC)").

The yellowing was determined, first, by drawing down a further film in a film thickness of 500 μm onto a glass plate and storing or curing it under standard conditions for 4 weeks, then lining half of the film with aluminum foil and exposing the film to daylight in the laboratory. After 3 months, the aluminum foil was removed and the yellowing on account of the observed color difference between the covered area and the free area of the film was assessed visually. Here, "none" means no perceptible color difference, "slight" refers to a small difference in color, "moderate" refers to a distinct difference in color, and "severe" refers to a severe difference in color.

A further measure used for the yellowing was the color change after exposure in a weathering tester. For this purpose, a further film was drawn down in a film thickness of 500 μm onto a glass plate and was stored, or cured, under standard conditions for 2 weeks and subsequently exposed in a Q-Sun Xenon Xe-1 weathering tester with Q-SUN Daylight-Q optical filter and with a xenon lamp, with a luminous intensity of 0.51 W/m² at 340 nm and at a temperature of 65° C. for 72 hours (Q-Sun (72 h)). Thereafter the color difference ΔE of the film thus exposed was determined in comparison to the corresponding unexposed film, using an NH310 colorimeter from Shenzen 3NH Technology Co. LTD, equipped with Silicon Photoelectric Diode Detector, Light Source A, Color Space Measurement Interface CIE L*a*b*C*H*. ΔE values of 0.5 to 1.5 here represent a small color difference, 1.5 to 3 a marked color difference, 3 to 6 a distinctly visible color difference, and more than 6 a large color difference.

The results are reported in tables 2 to 6.

The epoxy resin compositions Ex-1 to Ex-18 are inventive examples. The epoxy resin compositions Ref-1 to Ref-10 are comparative examples.

TABLE 2

Composition and properties of Ex-1 to Ex-3 and Ref-1 to Ref-2.

| Example | | Ex-1 | Ex-2 | Ex-3 | Ref-1 | Ref-2 |
|---|---|---|---|---|---|---|
| Resin comp.: | | | | | | |
| Araldite ® GY-250 | | 167.2 | 167.2 | 167.2 | 167.2 | 167.2 |
| Araldite ® DY-E | | 31.8 | 31.8 | 31.8 | 31.8 | 31.8 |
| Hardener comp.: | | | | | | |
| Amine | | 1 | 3 | 4 | | |
| | | 54.8 | 69.1 | 64.8 | — | — |
| Gaskamine ® 240 | | — | — | — | 103.0 | — |
| 1,3-bis(benzylamino-methyl)benzene | | — | — | — | — | 158.2 |
| Ancamine ® K54 | | 5.1 | 5.4 | 5.3 | 6.0 | 7.1 |
| Viscosity (10') [Pa · s] | | 0.48 | 0.47 | 0.60 | 0.68 | 0.34 |
| König | (1 d SC) | 41 | 11 | 39 | 70 | n.d. |
| hardness | (2 d SC) | 111 | 50 | 112 | 127 | 27 |
| [s] | (4 d SC) | 165 | 112 | 168 | 167 | 108 |
| | (7 d SC) | 185 | 147 | 197 | 179 | 146 |
| | (14 d SC) | 210 | 182 | 217 | 195 | 154 |
| Appearance (SC) | | attractive | attractive | attractive | attractive | attractive |
| Yellowing | | slight | slight | slight | severe | severe |
| König | (7 d 8°/80%) | 36 | 31 | 46 | 83 | 6 |
| hardness | (+2 d SC) | 151 | 119 | 147 | 133 | 78 |
| [s] | (+7 d SC) | 190 | 167 | 196 | 169 | 161 |
| | (+3 w SC) | 214 | 202 | 209 | 174 | 169 |
| Appearance (8°/80%) | | attractive | attractive | attractive | attractive | attractive |
| Number of marks | | 1 | 1 | 1 | 1 | 3 |

"n.d." stands for "not determined"

TABLE 3

Composition and properties of Ex-4 to Ex-7 and Ref-4 to Ref-6.

| Example | | Ex-4 | Ex-5 | Ex-6 | Ex-7 | Ref-4 | Ref-5 | Ref-6 |
|---|---|---|---|---|---|---|---|---|
| Resin comp.: | | | | | | | | |
| Araldite ® GY-250 | | 167.2 | 167.2 | 167.2 | 167.2 | 167.2 | 167.2 | 167.2 |
| Araldite ® DY-E | | 31.8 | 31.8 | 31.8 | 31.8 | 31.8 | 31.8 | 31.8 |
| Hardener comp.: | | | | | | | | |
| Amine | | 1A | 1D | 3D | 4D | 5 | 5D | — |
| | | 54.7 | 54.7 | 69.1 | 64.8 | 54.7 | 54.7 | |
| Gaskamine ® 240 | | — | — | — | — | — | — | 103.0 |
| Viscosity (10') [Pa · s] | | 0.34 | 0.30 | 0.47 | 0.43 | 0.57 | 0.36 | 0.60 |
| König | (1 d SC) | 21 | 61 | 104 | 73 | 14 | 38 | 29 |
| hardness | (2 d SC) | 87 | 137 | 172 | 153 | 25 | 53 | 77 |
| [s] | (4 d SC) | 141 | 185 | 203 | 186 | 50 | 70 | 113 |
| | (7 d SC) | 165 | 195 | 209 | 195 | 73 | 85 | 132 |
| | (14 d SC) | 186 | 209 | 209 | 207 | 127 | 101 | 143 |
| Appearance (SC) | | attractive | attractive | attractive | attractive | specks | hazy | attractive |
| Q-Sun (72 h) ΔE | | n.d. | 1.1 | n.d. | 3.5 | n.d. | 13.2 | 17.3 |

TABLE 3-continued

Composition and properties of Ex-4 to Ex-7 and Ref-4 to Ref-6.

| Example | | Ex-4 | Ex-5 | Ex-6 | Ex-7 | Ref-4 | Ref-5 | Ref-6 |
|---|---|---|---|---|---|---|---|---|
| König hardness [s] | (7 d 8°/80%) | 25 | 70 | 119 | 63 | 8 | 27 | 36 |
| | (+2 d SC) | 84 | 164 | 199 | 154 | 28 | 63 | 85 |
| | (+7 d SC) | 116 | 189 | 214 | 160 | 78 | 106 | 116 |
| | (+14 d SC) | 144 | 204 | 217 | 171 | 102 | 109 | 126 |
| Appearance (8°/80%) | | attractive | attractive | attractive | attractive | hazy | hazy | hazy |
| Number of marks | | 1 | 1 | 3 | 1 | n.m. | 2 | 1 |

"n.d." stands for "not determined"
"n.m." stands for "not measurable" owing to the hazy surface

TABLE 4

Composition and properties of Ex-8 to Ex-11 and Ref-3.

| Example | | Ex-8 | Ex-9 | Ex-10 | Ex-11 | Ref-3 |
|---|---|---|---|---|---|---|
| Resin comp.: | | | | | | |
| Araldite ® GY-250 | | 167.2 | 167.2 | 167.2 | 167.2 | 167.2 |
| Araldite ® DY-E | | 31.8 | 31.8 | 31.8 | 31.8 | 31.8 |
| Hardener comp.: | | | | | | |
| EP adduct 1 | | 65.7 | 65.7 | 65.7 | 65.7 | 65.7 |
| Amine | | 1 | 2 | 3 | 4 | — |
| | | 21.9 | 35.9 | 27.6 | 25.9 | — |
| Gaskamine ® 240 | | — | — | — | — | 41.2 |
| Ancamine ® K 54 | | 5.7 | 6.0 | 5.9 | 5.8 | 6.1 |
| Viscosity (10') [Pa · s] | | 2.17 | 2.05 | 2.13 | 2.22 | 2.42 |
| König hardness [s] | (1 d SC) | 48 | 25 | 56 | 83 | 102 |
| | (2 d SC) | 148 | 119 | 113 | 144 | 144 |
| | (4 d SC) | 171 | 150 | 148 | 174 | 164 |
| | (7 d SC) | 183 | 165 | 167 | 188 | 174 |
| | (14 d SC) | 200 | 179 | 179 | 203 | 192 |
| Appearance (SC) | | sl. matt | sl. matt | sl. matt | sl. matt | sl. matt |
| König hardness [s] | (7 d 8°/80%) | 57 | 48 | 63 | 73 | 59 |
| | (+2 d SC) | 144 | 113 | 136 | 154 | 136 |
| | (+7 d SC) | 183 | 147 | 168 | 186 | 161 |
| | (+3 w SC) | 196 | 169 | 197 | 209 | 174 |
| Appearance (8°/80%) | | sl. matt | sl. matt | sl. matt | sl. matt | sl. matt |
| Number of marks | | 1 | 1 | 1 | 1 | 1 |

"sl." stands for "slightly"

TABLE 5

Composition and properties of Ex-13 to Ex-16 and Ref-7 to Ref-8.

| Example | | Ex-13 | Ex-14 | Ex-15 | Ex-16 | Ref-7 | Ref-8 |
|---|---|---|---|---|---|---|---|
| Resin comp.: | | | | | | | |
| Araldite ® GY-250 | | 167.2 | 167.2 | 167.2 | 167.2 | 167.2 | 167.2 |
| Araldite ® DY-E | | 31.8 | 31.8 | 31.8 | 31.8 | 31.8 | 31.8 |
| Hardener comp.: | | | | | | | |
| EP adduct 2 | | — | 42.6 | 42.6 | — | 42.6 | — |
| EP adduct 3 | | 36.0 | — | — | — | — | — |
| Jeffamine ® D-230 | | 24.0 | 24.0 | 24.0 | 12.0 | 24.0 | 12.0 |
| Amine | | 1D | 1D | 1D | 1D | | |
| | | 11.0 | 11.0 | 11.0 | 43.8 | — | — |
| Gaskamine ® 240 | | — | — | — | — | 20.6 | 82.4 |
| Salicylic acid | | — | — | 1.6 | — | — | — |
| Ancamine ® K 54 | | — | — | 1.6 | — | — | — |
| Viscosity (10') [Pa · s] | | 0.82 | 0.82 | 1.13 | 0.26 | 0.96 | 0.60 |
| König hardness [s] | (1 d SC) | 35 | 38 | 55 | 38 | 31 | 15 |
| | (2 d SC) | 109 | 76 | 129 | 129 | 78 | 61 |
| | (4 d SC) | 161 | 148 | 163 | 176 | 126 | 104 |
| | (7 d SC) | 179 | 168 | 177 | 195 | 151 | 130 |
| | (14 d SC) | 193 | 184 | 191 | 209 | 167 | 139 |
| Appearance (SC) | | attractive | attractive | attractive | attractive | attractive | attractive |
| Q-Sun (72 h) ΔE | | 1.4 | 2.8 | 10.4 | 1.7 | 7.2 | 14.8 |
| König hardness [s] | (7 d 8°/80%) | 40 | 26 | 44 | 27 | 28 | 26 |
| | (+2 d SC) | 122 | 90 | 137 | 76 | 97 | 77 |
| | (+7 d SC) | 161 | 102 | 153 | 105 | 136 | 116 |
| | (+14 d SC) | 168 | 119 | 156 | 108 | 144 | 127 |
| Appearance (8°/80%) | | attractive | attractive | attractive | attractive | attractive | attractive |
| Number of marks | | 1 | 1 | none | 1 | 1 | 1 |

TABLE 6

| | Ex-17 | Ex-18 | Ref-9 | Ref-10 |
|---|---|---|---|---|
| Composition and properties of Ex-17 to Ex-18 and Ref-9 to Ref-10. | | | | |
| Example | | | | |
| Resin comp.: | | | | |
| Araldite ® GY-250 | 167.2 | 167.2 | 167.2 | 167.2 |
| Araldite ® DY-E | 31.8 | 31.8 | 31.8 | 31.8 |
| Hardener comp.: | | | | |
| EP adduct 2 | 53.3 | — | — | — |
| EP adduct 3 | — | 45.0 | 45.0 | 45.0 |
| Amine | 1D | 1D | 5D | — |
| | 27.4 | 27.4 | 27.4 | |
| Gaskamine ® 240 | — | — | — | 51.5 |
| Viscosity (10') [Pa · s] | 1.35 | 1.28 | 1.39 | 1.66 |
| König (1 d SC) | 78 | 67 | 62 | 43 |
| hardness (2 d SC) | 133 | 143 | 109 | 87 |
| [s] (4 d SC) | 168 | 180 | 147 | 134 |
| (7 d SC) | 182 | 192 | 171 | 148 |
| (14 d SC) | 196 | 206 | 187 | 175 |
| Appearance (SC) | attractive | attractive | attractive | attractive |
| Q-Sun (72 h) ΔE | 3.2 | 1.7 | 3.7 | 5.0 |
| König (7 d 8°/80%) | 55 | 60 | 43 | 14 |
| hardness (+2 d SC) | 158 | 170 | 132 | 119 |
| [s] (+7 d SC) | 182 | 192 | 173 | 157 |
| (+14 d SC) | 189 | 197 | 186 | 176 |
| Appearance (8°/80%) | attractive | attractive | attractive | attractive |
| Number of marks | 1 | 1 | 2 | 1 |

The invention claimed is:

1. Method comprising hardening epoxy resins with formula (I)

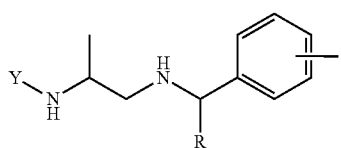

where

Y is a hydrogen radical or a radical of the formula

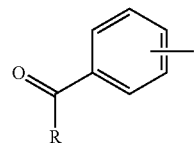

and n is 0 or 1 or 2 or 3,

R is a hydrogen radical or is methyl or phenyl, and

X is identical or different radicals selected from the group consisting of alkyl, alkoxy and dialkylamino having in each case 1 to 18 carbon atoms.

2. The method as claimed in claim 1, wherein R is a hydrogen radical or is methyl.

3. The method as claimed in claim 1, wherein Y is the radical of the formula

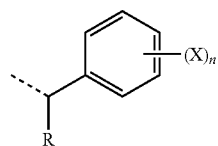

in which n is 0.

4. The method as claimed in claim 1, wherein Y is the radical of the formula

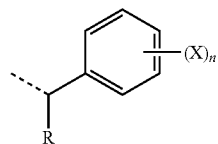

in which R is a hydrogen radical and n is 0.

5. The method as claimed in claim 1, wherein Y is the radical of the formula

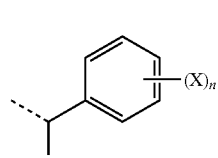

in which n is 1 and X is methoxy or is dimethylamino.

6. A reaction product from the reductive alkylation of 1,2-propylenediamine with at least one aldehyde or ketone of the formula (II) and hydrogen, comprising at least one amine of the formula (I) as described in claim 1 as hardener for epoxy resin

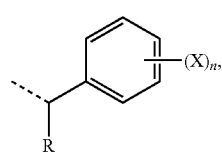

where R is a hydrogen radical or is methyl or phenyl.

7. A hardener for epoxy resins, comprising at least one amine of the formula (I) as described in claim 1 and at least one further amine and/or at least one accelerator.

8. The hardener as claimed in claim 7, wherein the accelerator is salicylic acid or 2,4,6-tris(dimethylaminomethyl)phenol or a combination thereof.

9. The hardener as claimed in claim 7, wherein the further amine comprises at least one adduct of (i) at least one polyamine, having at least three amine hydrogens reactive toward epoxide groups, with (ii) at least one epoxide.

10. The hardener as claimed in claim 7, wherein 1 to 95 weight % of amine of the formula (I) is present.

11. The hardener as claimed in claim 7, wherein it contains not more than 5 weight % of unincorporable diluents.

12. An epoxy resin composition comprising
a resin component comprising at least one epoxy resin and
a hardener component comprising at least one amine of the formula (I) as described in claim 1.

13. A coating comprising an epoxy resin composition as described in claim 12.

14. A cured composition obtained from the curing of an epoxy resin composition as claimed in claim 12.

15. A method for the dilution of a hardener for epoxy resins and/or of an epoxy resin, wherein an amine of the formula (I) as described in claim 1 is added.

16. The method as claimed in claim 1, wherein Y is the hydrogen radical.

* * * * *